United States Patent [19]

Jouillat et al.

[11] Patent Number: 5,024,355

[45] Date of Patent: Jun. 18, 1991

[54] DEVICE FOR DISPENSING A LIQUID OR A CREAM IN SMALL-VOLUME DROPS, AND AN ASSOCIATED DISPENSING ASSEMBLY

[75] Inventors: Claude Jouillat, Montigny Sur Avre; Michel Brunet, Sainte Colombe La Commanderie, both of France

[73] Assignee: Societe Technique de Pulverisation—STEP, Paris, France

[21] Appl. No.: 454,652

[22] Filed: Dec. 20, 1989

[30] Foreign Application Priority Data

Dec. 20, 1988 [FR] France .................... 88 16867
Apr. 6, 1989 [FR] France .................... 89 04538

[51] Int. Cl.$^5$ .................................................... B67D 5/64
[52] U.S. Cl. ................................ 222/162; 222/340; 222/422; 417/552
[58] Field of Search ............. 222/181, 185, 383, 385, 222/321, 340, 420, 422, 514, 162, 183; 604/300; 417/489, 552; 239/333

[56] References Cited

U.S. PATENT DOCUMENTS

| | | | |
|---|---|---|---|
| 2,117,296 | 5/1938 | Cahoon | 222/340 X |
| 2,281,051 | 4/1942 | Roger | 222/422 X |
| 3,187,960 | 6/1965 | Gorman | 222/340 X |
| 3,302,834 | 2/1967 | Alsop | 222/162 |
| 3,488,002 | 1/1970 | Mina | 222/185 X |
| 4,273,290 | 6/1981 | Quinn | 239/333 X |
| 4,722,459 | 2/1988 | Goncalves | 222/340 X |
| 4,908,024 | 3/1990 | Py | 604/300 |

Primary Examiner—Michael S. Huppert
Assistant Examiner—Gregory L. Huson
Attorney, Agent, or Firm—Sughrue, Mion, Zinn, Macpeak and Seas

[57] ABSTRACT

The present dispenser device is designed in particular for eye treatment and comprises a pump body including a pump chamber, a piston slidable within the chamber and extended beyond the chamber by a rod pierced by a channel capable of communicating with the chamber, and an endpiece fixed to the rod and having a dispensing orifice in line with the channel of the rod. In addition to the above conventional items, the dispenser has a chamber admission valve which is constituted by co-operation between the enclosure defining the pump chamber and the piston which engages therein or projects therefrom as the case may be. The co-operation is preferably via a sealing lip. This disposition makes it possible to dispense a drop whose volume as determined by the capacity of the chamber is very small. In addition, the piston is returned to its rest position with the admission valve closed by resilient means disposed between the pump body and the endpiece. This guarantees that only drop is dispensed at a time. Finally, an outlet valve is placed between the end of the channel in the rod and the dispensing orifice of the endpiece in order to ensure that a dispensed drop is slightly precompressed. The dispenser device is advantageously integrated in a dispenser assembly comprising a supply of substance to be dispensed together with a housing facilitating actuation of the assembly by a user. Some designs of assembly are particularly attractive, from the economic point of view, with respect to the process of being filled with the substance to be dispensed.

27 Claims, 9 Drawing Sheets

DEVICE FOR DISPENSING A LIQUID OR A CREAM IN SMALL-VOLUME DROPS, AND AN ASSOCIATED DISPENSING ASSEMBLY

The present invention relates to an assembly containing a supply of a substance whose consistency may run from that of water or that of a cream, the assembly including a device for enabling the substance to be dispensed drop-by-drop. In addition, each drop corresponds to a small volume of about 10 microliters. Finally, the drop is ejected at a pressure which is slightly greater than atmospheric pressure so that it is possible to obtain a drop-dividing effect.

BACKGROUND OF THE INVENTION

Such a dispensing assembly is particularly advantageous for ophthalmological treatments. This is because 5 to 10 microliters ($\mu l$ or $mm^3$) suffice for washing the surface of the eye. Even the finest of normal droppers deliver drops whose volume is too great. As a result, excess liquid deposited on the cornea runs into cavities and over nasal mucus membranes. This constitutes a loss of active substance, and may even be counter-indicated. The present invention therefore seeks to provide a device capable of generating and delivering a drop of very small volume, about 10 $mm^3$ or less.

Another aim of the invention is to provide a device that guarantees delivering only one drop at a time. The finest of presently-available droppers often suffer from the following drawback: they are difficult to operate, and if the user maintains pressure a little too long on a rubber bulb, for example, then a large number of drops are delivered almost simultaneously. This risk is increased when the user is in an uncomfortable position while operating the dropper, as is the case for eye treatments.

Finally, the present invention seeks to provide a dispensing assembly which includes not only a dispenser device having the above-mentioned qualities, but also a supply of substance commensurate with the operation of the device. Given the very small volume of the drops dispensed, the supply must also be small in size. This gives rise to a problem in the ease with which the dispensing assembly can be handled.

SUMMARY OF THE INVENTION

These various preoccupations are solved firstly by means of a dispenser device for dispensing a liquid or cream type substance in the form of small volume drops, the device comprising:

a pump body having a pump chamber formed therein with a bottom wall and an enclosure whose end furthest from said bottom wall is open;

a piston adapted to engage inside said enclosure via said open end and to slide in sealed manner therein between a high, admission position for admitting said substance into said chamber and a low, rest position, said piston being fixed to a rod of smaller diameter which passes in sealed manner through said bottom wall of said chamber and has a free end extending outside said pump body, said rod being pierced by a central channel communicating with a duct opening out laterally beneath said piston;

an endpiece having a dispensing orifice and adapted to be fastened in sealed manner to said free end of said rod extending outside said pump body in such a manner that said central channel faces said orifice;

resilient means disposed between said pump body and said endpiece in order to return said piston to said low, rest position in which it comes into abutment against said bottom wall of said chamber; and an outlet valve disposed between said central channel of said rod and said dispensing orifice of said endpiece.

In a first variant of the present dispenser device, said enclosure flares from its open end towards said bottom wall of said chamber such that once said piston engaged in said enclosure, sealing contact is established around a line only, said duct opening out at the root of said piston.

Said enclosure may alternatively be a right cylinder, said piston being enveloped by a flexible cylindrical gasket provided on its outside with an annular sealing lip directed towards said bottom wall of said chamber such that said lip co-operates with said enclosure in order to delimit said pump chamber, with at least one groove extending axially inside said enclosure from said open end down to a height such that said lip faces said at least one groove when said piston is in its high, admission position. In this case, said gasket advantageously has a bottom pierced by a hole adapted to receive said rod, said duct opening out laterally beneath said bottom of said gasket, and said gasket extending beyond said piston so that said gasket is firmly retained on said piston.

In this second variant, abutment means are disposed, where appropriate, between said pump body and said endpiece in order to limit the stroke of said piston between its low, rest position and its high, admission position. It is also possible to provide for a flexible pocket to be fixed in sealed manner around said enclosure in order to receive a supply of said substance and protect it from the air. In which case, it is advantageous for said enclosure to have an external annular thickening and for said pocket to have an opening with a reinforced edge, said opening being adapted to engage in a sealed fit around said enclosure.

Both in the first variant and in the second variant, said pump body preferably includes a sealing sleeve directed towards the outside of said body in order to bear against said rod passing through said bottom wall of said chamber. It may then be advantageous for said pump body to be made of a plastic material whose flexibility is comparable with that of low density polyethylene, said body also including a fine sealing lip directed towards the inside of said chamber in order to bear against said rod passing through said bottom wall, said rod having an annular cut-out into which said lateral duct opens out.

For example, said endpiece may comprise a hollow tube having an open end, said free end of said rod being adapted to snap-fasten within said open end of said hollow tube. In this case, said outlet valve may occupy the bottom of said hollow tube in said endpiece and may be constituted by two identical hemispheres with at least one flexible spacer extending therebetween, one of the hemispheres co-operating with the opening of said central channel, and the other hemisphere co-operating with said dispensing orifice.

Advantageously, said resilient means are constituted by a helical spring and said endpiece also includes an outer annular wall for holding and fixing said spring around said hollow tube. In which case said high position of said piston is advantageously determined by the said free end of said hollow tube of said endpiece coming into abutment against said pump body.

However, it is equally advantageous for said resilient means to be constituted by a helical spring and said spring to be held around said hollow tube by radial partitions integral with said endpiece. In which case, said high position of said piston is advantageously determined by said radial partitions fixed to said endpiece coming into abutment against said pump body.

It may also be advantageous for said dispensing orifice to form a portion of a nozzle integrated in said endpiece.

Advantageously, the maximum volume of said pump chamber, equal to the product of the section of said piston multiplied by its stroke, i.e. the distance between its high position and its low position, is greater than the sum of the volume of said central channel and said radial duct of said rod. In which case the volume of a dispensed drop may lie in the range 5 mm$^3$ to 25 mm$^3$, and preferably in the range 5 mm$^3$ to 10 mm$^3$.

The problems outlined in the introduction are also solved by a dispenser assembly including a dispenser device as outlined above, wherein said pump body is crimped onto a flask which has a bottom and which encloses a supply of said substance protected from the air.

In another embodiment of the present dispenser assembly including a dispensing device as outlined above, said pump body extends around said enclosure defining said pump chamber to constitute a receptacle which is open at its end furthest from said pump body in order to receive a supply of said substance protected from the air, said end of said receptacle being closed by closure means for forming a bottom on said dispenser assembly.

In this case, said receptacle flares away from said enclosure to constitute a truncated cone such that there exists a minimum inside volume between said receptacle and said enclosure.

Still with this other embodiment of the present dispenser assembly, said closure means of said receptacle may be constituted by a capsule which is crimped on after said receptacle has been filled to about one half its capacity with the substance. However, said closure means of said receptacle may alternatively be constituted by a snap-on cap, with an air vent being provided between said open end of said receptacle and said cap, and a scraper piston also being engaged in sealed manner inside said receptacle in order to separate said substance from the ambient air regardless of how full said receptacle may be.

In a further embodiment of the present dispenser assembly including a dispensing device as outlined above, said pump body is adapted to receive in sealed manner and by snap-fastening a cartridge having a bottom and an open end opposite to said bottom, an air vent being provided through said bottom, a supply of said substance initially being contained inside said cartridge between a diaphragm closing said open end and a scraper piston disposed adjacent to said bottom, said piston also having a punch-forming face suitable for puncturing said diaphragm on the first occasion said dispenser device is actuated.

For any of these various embodiments, a housing may receive said dispenser device together with said supply of substance, said housing being adapted to leave said dispensing orifice disengaged and also to leave said bottom disengaged, and being of such a shape as to enable a user applying two fingers of one hand against said housing to be able to press against said bottom with another finger of the same hand in order to actuate said dispenser device. Another solution may provide for said endpiece to extend around said rod of said piston in the form of a shell suitable for receiving said supply of said substance while leaving said bottom disengaged, said shell including grasping means, thereby enabling a user to apply two fingers of one hand thereagainst while pressing with another finger of the same hand against said bottom so as to actuate said dispenser device.

In any event, it is advantageous for said bottom initially to comprise tear-off tamperproofing tongues projecting laterally in order to constitute an abutment for said supply and prevent said dispenser device being actuated.

BRIEF DESCRIPTION OF THE DRAWINGS

The following description refers to the accompanying drawings and relates to two variants of the dispenser device and four embodiments of the dispenser assembly, all given by way of non-limiting example. In the accompanying drawings these examples are all shown at a scale considerably greater than lifesize. In the drawings.

In the various figures, parts or portions of parts that perform the same function are given identical reference numerals even if they are structurally different from one embodiment to another.

DETAILED DESCRIPTION

Figure 1:
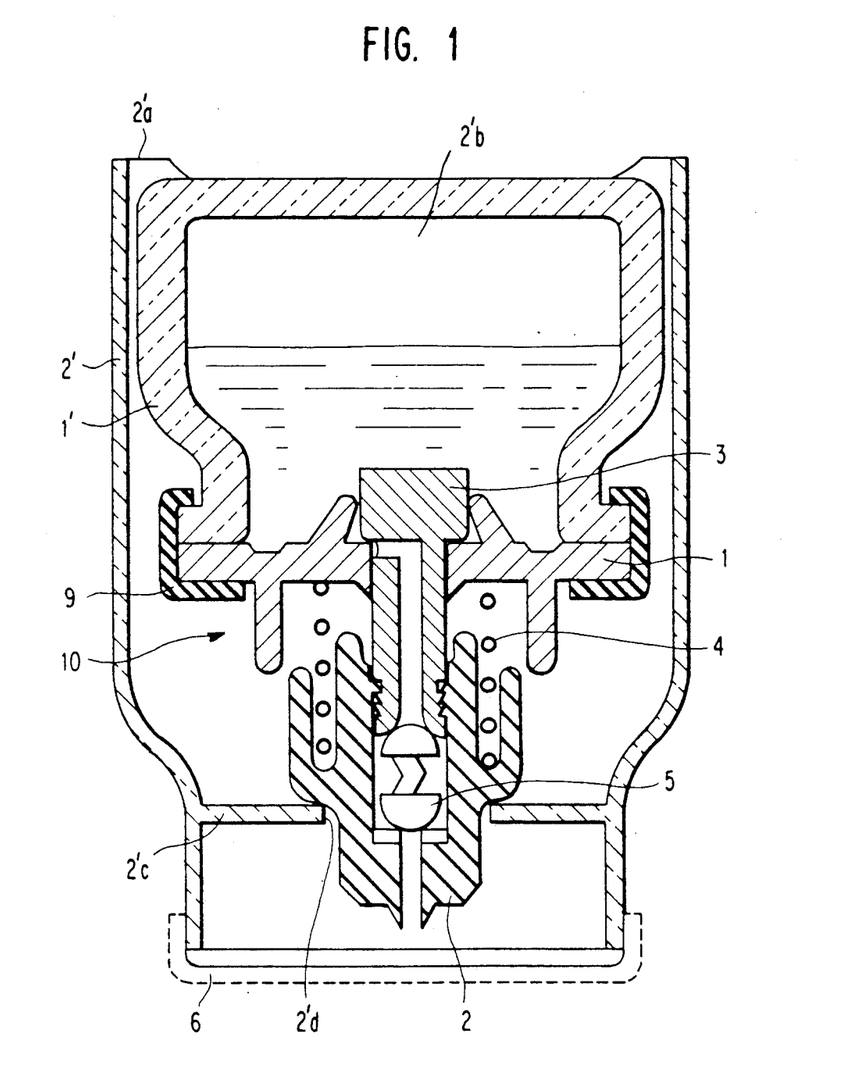
FIG. 1 is an axial section through a first variant of the present dispenser device in its rest position, and it is shown in association with a first embodiment of the present dispenser assembly.

A first embodiment of a dispenser assembly in accordance with the invention is shown in diagrammatic sections in FIG. 1. It comprises a flask 1' shown in its in-use position, bottom end uppermost. A liquid level can be seen inside the flask 1'. The flask is disposed in an outer housing 2' provided with a cap 6. The flask 1' is made of glass or plastic and has a first version of the dispenser device 10 crimped thereto by means of a ring 9. The crimping connection of the device 10 on the flask 1' is shown as having no sealing washer, however, depending on the material used for manufacturing the device 10, it may be preferable to use a washer.

Figure 2:
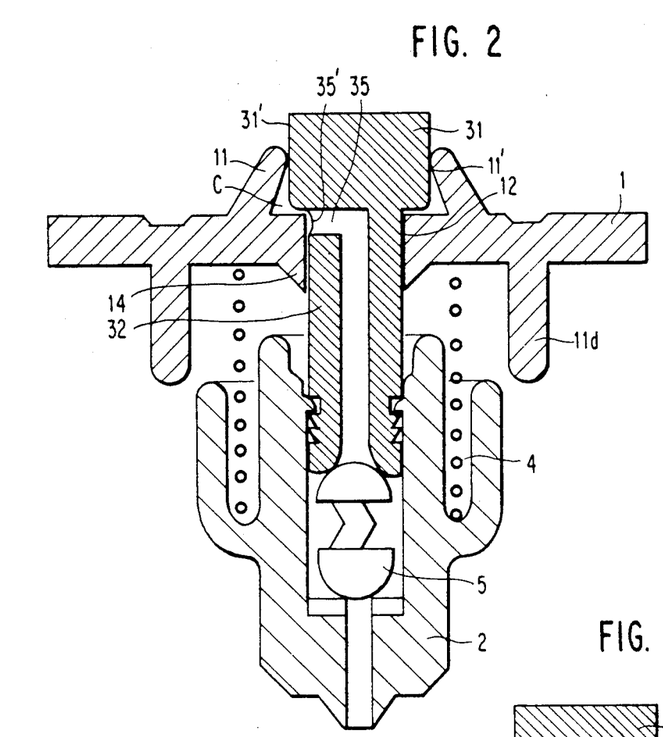
FIGS. 2 to 5 are axial sections through the variant shown in FIG. 1, with these figures showing only the dispenser device of the present invention and serving to illustrate different stages in the operation of the device.
Figure 3:
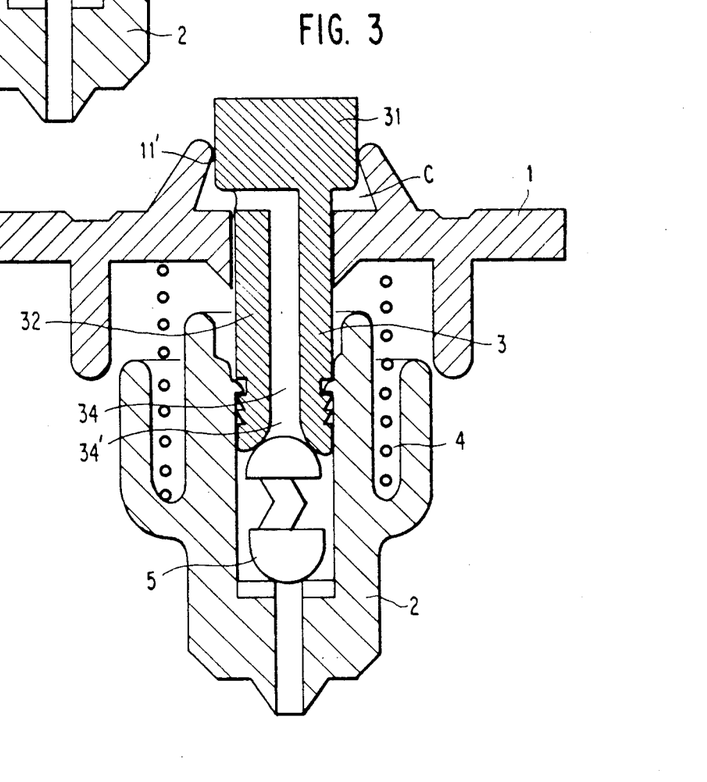

The device 10 is shown on a larger scale in FIGS. 2 to 5. It comprises five parts: a fixed part 1 (relative to the flask) referred to below as a "pump body"; and a moving assembly comprising three parts: a rod-piston 3; an endpiece 2; and a non-return valve 5 between them; and finally a spring 4 maintaining the moving assembly in a "rest" position relative to the pump body, as shown in FIG. 2.

Figure 6:
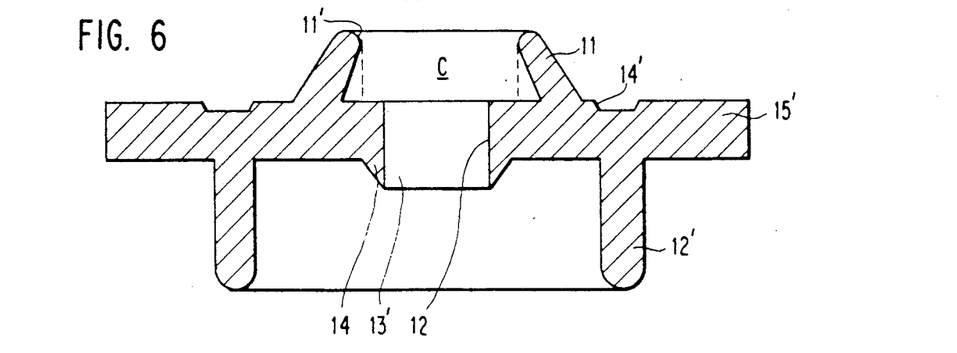
FIGS. 6, 7, and 8 are axial sections through respective components of the FIG. 1 variant of the dispenser device of the invention.
Figure 7:
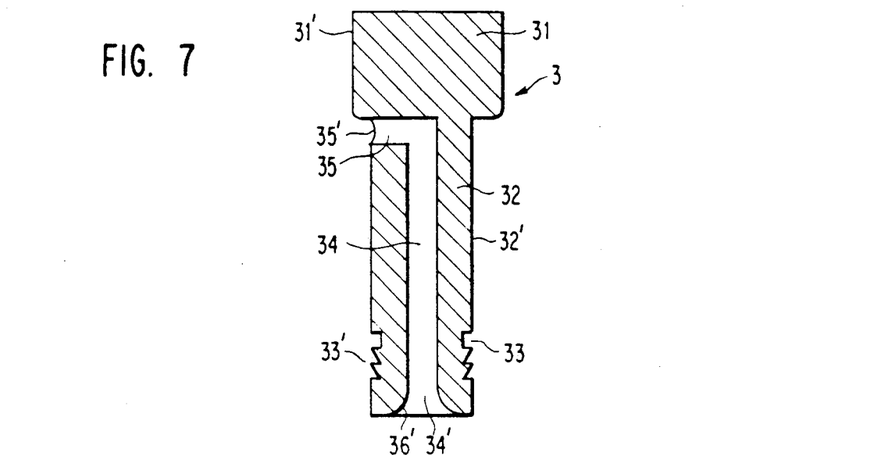

The pump body is generally in the form of a hollow round part (see cross-section of FIG. 6). Its outer rim 15' is used for fixing the dispenser device 10 to the neck of a flask, and it constitutes a sealing washer if it is molded in a suitable material, such as polyethylene, for example. The base of the pump body is pierced by a central hole 13' in which the rod-piston 3 is slidably mounted (see FIG. 7). Since this sliding must be sealed, the hole is molded accurately, and one or both edges of the hole 13 may be provided with a circular sealing lip 14. When sealed in this way, the flask does not include an air vent. The base of the pump body 1 has a skirt 12' on its face directed away from the flask, the skirt being useful for centering the crimping ring during assembly, and serving to protect the spring 4 and the rod-piston 3 from dirt. An enclosure 11 is provided on the face of the body 1 facing towards the inside of the flask, with the wall of the enclosure 11 being in the form of a skirt directed in the opposite direction to the skirt 12' and having a sliding surface adapted to co-operate, in this first variant of the dispenser device of the invention, directly with the side surface 31' of the head 31 of the rod-piston 3. This surface could be cylindrical as shown in dashed lines. However, in the example shown, the contact surface with the piston is reduced to a circular line of contact 11' on a toroidal surface which seals against the piston. Thus, the enclosure 11 and the piston together define a pump chamber C. A circular groove 14' for facilitating molding is shown on the top surface of the base of the pump body 1 (FIG. 6).

The rod-piston 3 (FIG. 7) comprises a head 31 constituting the piston per se and a rod 32, both of which are circular in section with the rod being smaller in diameter than the piston. The diameter of the rod is equal to the diameter of the hole 13' through the base of the body 1 so as to slide therein while providing sealing between the two sides of the base. The diameter of the head of the piston is equal to the diameter of the enclosure 11 formed on the top face of the base of the body 1. The piston head can thus slide in the enclosure while providing sealing between the two spaces separated by the contact surface. The rod of the piston has an axial blind channel 34 extending from its end furthest from the head (bottom end) to the head. At this point, the axial channel 34 communicates with the outside via a radial duct 35 opening out via an opening 35' placed immediately beneath the head and, as explained above, of smaller diameter than the head. The opening 34' at the bottom end is advantageously flared and is preferably placed in the center of the rod in order to constitute a seat for the non-return valve 5. In the variant of the present dispenser device shown in FIGS. 1 to 8, the non-return valve comprises two half-balls interconnected by a zig-zag spacer. This makes it symmetrical, thereby facilitating assembly of the dispenser device 10. Finally, the bottom of the rod 32 of the piston is formed with snap-fastening grooves 33.

Figure 8:
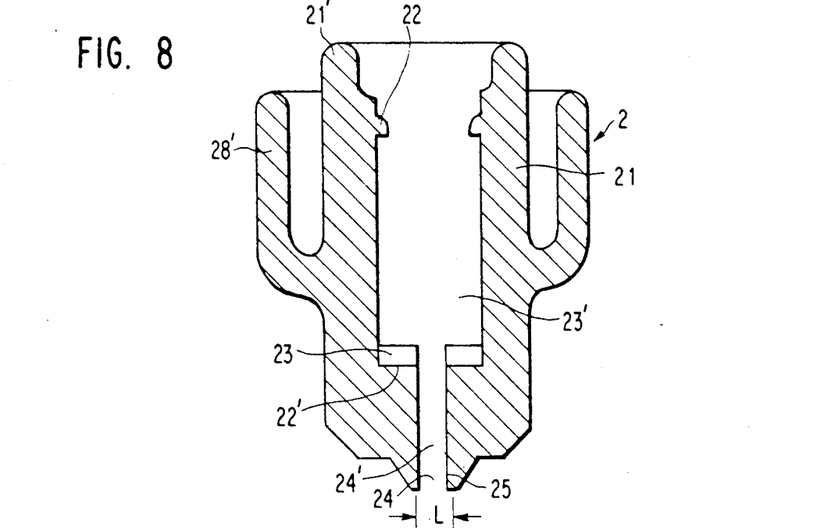

FIG. 8 is a section view through the endpiece 2. Its main shape is tubular, defined by a hollow tube 21 delimiting a cylindrical chamber 23' and designed to receive the bottom end 33' of the rod-piston 3. The top portion of the inside wall of the hollow tube 21 is provided with one or more snap-fastening ridges 22 for co-operating with the grooves 33 of the rod-piston. In order to fix these two parts together, the bottom end 33' of the rod-piston 3 is inserted into the chamber 23' of the endpiece 2, and is pushed home until snap-fastening occurs. The rod-piston is inserted in this way after being passed through the central hole 13' in the base of the pump body 1. The three-part assembly comprising the pump body, the rod-piston, and the endpiece is then inseparable. The non-return valve 5 should previously have been placed in the bottom of the cylindrical chamber 23', and the spring 4 should have been placed around the rod-piston 3 between the rod-piston and the endpiece. When the non-return valve is of the preferred shape, as shown, it automatically takes up a correct position. All five parts are then inseparable. Together they constitute a dispenser device 10 of the invention which is ready for mounting on a flask.

In the chamber 23' in the endpiece 2, towards its end furthest from the end into which the rod-piston 3 is engaged, there is a step 22' defining a passage 24' passing through the bottom of the chamber. On the outside face of the endpiece, the outlet 24 from the passage is surrounded by a projection 25 for obtaining an appropriate diameter for releasing drops. The total width L of the orifice 24 and of the annular chamfered projection 25 surrounding it is defined as a function of the capillary properties of the liquid to be dispensed and of the surface of the endpiece, and also as a function of the desired volume for each drop. By way of example, for an endpiece made of polyethylene, used for dispensing water, in drops having a volume of 10 mm$^3$, the width L should be not more than 0.7 mm.

In order to facilitate liquid emission, radial fluting 23 is provided in the bottom of the chamber 23' on the step 22'.

Finally, the endpiece includes an outer, second cylindrical wall 28' which provides an abutment and a guide for the spring, and which also serves, in co-operation with the skirt 12' on the base of the pump body, to protect the spring. The dimensions are chosen (see FIG. 2) in order to ensure that there is as little clearance as possible between the edges of the wall 28' and of the skirt 12', while ensuring that they move freely. Preferably, the wall 28' penetrates into the skirt 12'.

The operation of this first embodiment of a dispenser assembly in accordance with the invention is now described with reference to FIGS. 2 to 5.

The user seeks to dispense a drop of liquid from the dispenser assembly shown in section in FIG. 1. In practice, given the size of the drops to be dispensed, namely 10 mm$^3$, the receptacle must be relatively small since otherwise it would take years to use up the substance contained therein. Unfortunately, ophthalmological substances should not be kept for more than 15 days after the flask has been opened. The supply should therefore have a volume of 1 to a few cubic centimeters (1 cm$^3$ = 100 times 10 mm$^3$). It will therefore be understood that FIG. 1 is drawn greater than lifesize (about 4 to 5 times greater). In an advantageous example, the flask has a volume of 1.5 cm$^3$, containing 1 cm$^3$ of liquid and 0.5 cm$^3$ of air.

In order to operate the flask shown in FIG. 1, the flask is turned upsidedown after removing its cap 6 and the endpiece 2 is then pressed towards the flask 1'. This is done by pressing with a finger (thumb or index finger)

on the bottom of the flask and pressing with two other fingers on the endpiece, preferably via the housing 2' since it provides a larger area to grip than does the small endpiece. It may be observed that the housing 2' which is normally sold with the flask and remains thereon, does not have a bottom, thereby leaving free access to the bottom of the flask, and it is advantageously provided with at least one and preferably with two diametrically opposite extensions 2'a separated by cut-outs 2'b. They prevent the flask from being stood on its bottom, thereby ensuring that when it is put down, it is stood on its endpiece end, thereby making it more difficult to loose pump priming. The housing 2' comprises a wall 2'c having an orifice 2'd through which the end of the endpiece projects, thereby enabling the endpiece to be pushed towards the flask.

For the following operations, reference is made to FIGS. 2 to 5 which show the dispenser device on its own without the flask and without the housing. In these figures, the device is directed downwards with its endpiece bottommost and with the flask above the device.

In the starting position (FIG. 2) referred to below as the low, rest position, the head 31 of the rod-piston bears against the bottom wall of the chamber C on the edge of the hole 13' through the base of the pump body. The rod 32 of the rod-piston is received in the hole in sealing contact reinforced by the sealing lip 14. The opening 35' of the radial duct 35 in the rod-piston faces the cylindrical wall 12 of the hole 13 through the base, and is therefore closed. The device is held resiliently in this position by the spring 4. The side surface 31' of the piston head 31 is in sealing contact with the edge of the enclosure 11 defining the pump chamber C.

If the moving assembly (rod-piston 3 and endpiece 2 together with the interposed non-return valve 5) is now raised, the piston head 31 slides within the pump chamber C. In the drawings, contact between the head and the enclosure is provided only around a circular line 11' in order to facilitate the manufacture, assembly, and operation, of a device which is discarded after being used a few times. The piston head comes away from the bottom wall of the chamber C, and the volume of the chamber C beneath the line of contact 11' increases, thereby setting up suction therein (see FIG. 3). At the other end of the axial channel 34 along the rod 32, the integrally molded plastic non-return valve 5 which is slightly compressed on assembly bears resiliently against the flared opening 34' of the channel. Suction is therefore established in the volume constituted by the channel 34, the radial duct 35, and the chamber C.

Figures 4, 5:
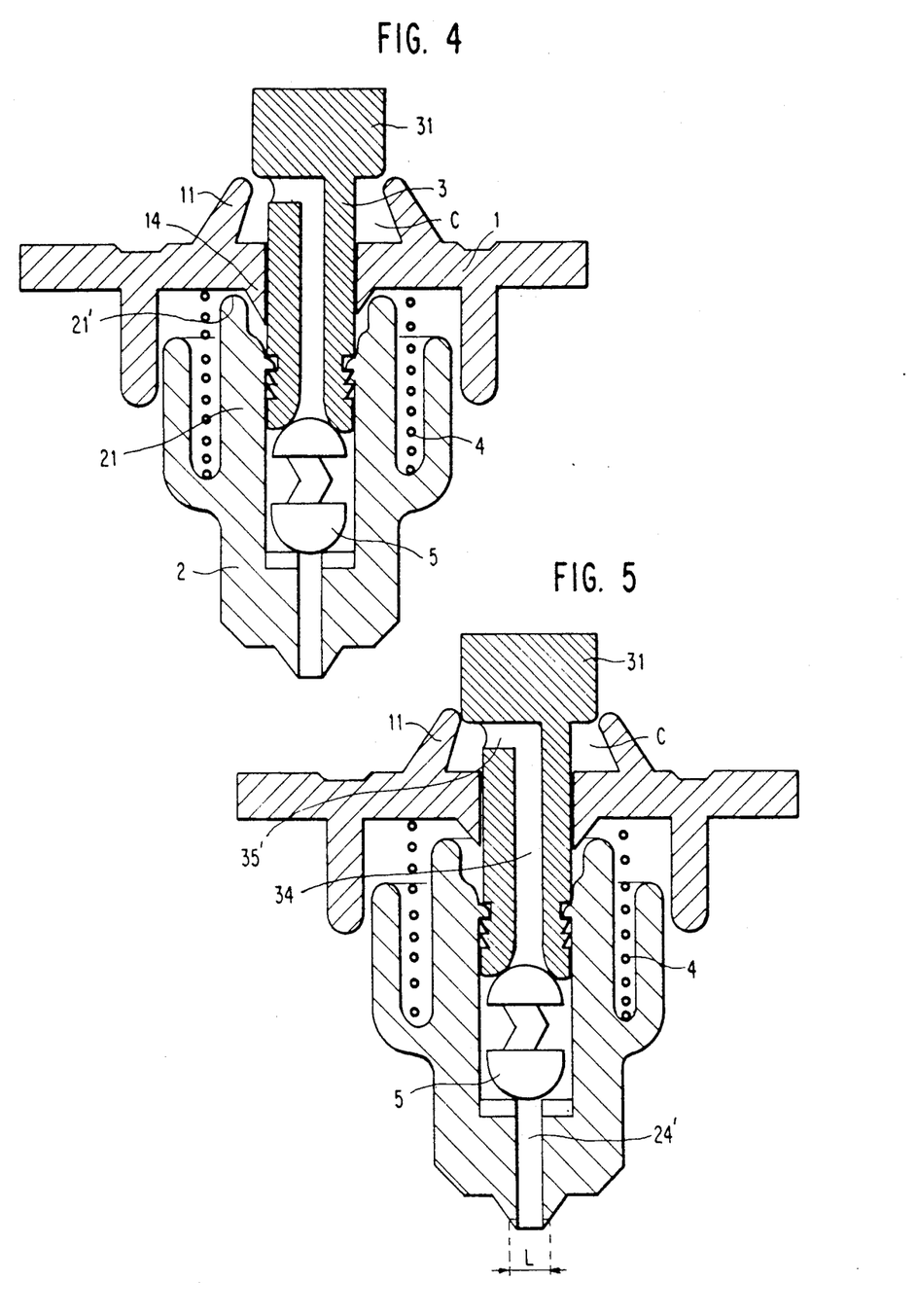

By continuing the upwards motion of the moving assembly, the volume of the chamber C is further increased, with suction therein also increasing, until the piston head 31 looses contact with the chamber 11 defining the pump chamber (FIG. 4). By virtue of the suction, the annular chamber C fills with liquid through the annular opening between the piston head and the edge of the enclosure while the piston reaches the top end of its stroke (high, admission position) by virtue of the top edge 21' of the endpiece 2 coming into contact with the bottom surface of the base of the body 1, in the vicinity of the sealing lip 14. At this point, nothing has yet come out of the endpiece. The volume of the chamber C, and more precisely the increase in its volume during the stroke of the piston, is equal to the product of the section of the piston multiplied by the axial distance between the low, rest position of the piston and the high, admission position thereof.

The user then releases finger pressure and the spring returns the moving assembly towards its rest position. Initially, the bottom edge of the piston head 31 engages in the enclosure 11 defining the pump chamber and the volume of the annular chamber C is confined. The chamber C is now closed (FIG. 5). The moving assembly continues to move down under thrust from the spring 4. The pressure rises inside the volume constituted by the chamber C, the channel 34, and the duct 35. This increased pressure lifts the valve 5 off the flared opening 34' of the axial channel, and the volume of the chamber C is ejected via the passage 24' of the endpiece. At the end of its stroke, the extra thickness of the piston bears against the bottom wall of the pump chamber whose volume thus becomes substantially zero. The ejected drop comes off if the outside diameter L of the endpiece orifice is small enough, as mentioned above.

In order to facilitate pump priming (and ensure that it happens automatically), the dimensions are defined so that the volume of the channel 34 is less than the volume of the chamber C. The volume of the chamber C is equal to the volume of the drop to be dispensed. In accordance with the invention, this volume should lie in the range 5 mm$^3$ to 25 mm$^3$, and preferably in the range 5 mm$^3$ to 10 mm$^3$. If the volume of the chamber C is selected to be 10 mm$^3$, then there will be no difficulty in making a channel whose volume is 7 mm$^3$. The first time the dispenser is operated, the chamber C fills with 10 mm$^3$ of liquid, and on being evacuated via the dispenser endpiece, these 10 mm$^3$ expel all of the 7 mm$^3$ of air. If a smaller chamber is desired, e.g. 5 mm$^3$, then the volume of the channel should be limited to 3 mm$^3$ or 4 mm$^3$.

Drop expulsion is under the control of the spring, and therefore takes place at a speed and under conditions which can be accurately determined and selected. The drop is expelled during the return stroke towards the rest position. While the user is exerting pressure on the device, nothing comes out. There is therefore no danger of several drops being ejected therefrom because the user is trembling (given that the user is holding the apparatus a few centimeters away from the eye in order to receive a drop therein).

It may also be observed that the polluted volume beneath the non-return valve is very small: a small fraction of a drop. By encouraging the use to stand the flask head down, the two extensions 2'a on the housing prevent liquid that may be polluted from running back into the flask.

Under no circumstances does the dispensed substance come into contact with a spring or a sealing gasket of any kind. The device thus guarantees sterile conditions. In addition, it may be radiation-sterilized if the materials from which it is made are suitably chosen.

It cannot be made to dispense liquid in any position other than the design utilization position. As appears more clearly in the description of other embodiments of the present dispenser assembly, the shape of the base of the pump body can be formed in a variant so as to use up all of the substance to be dispensed. There is no possibility of the pump becoming unprimed.

By dispensing very small doses of substance, it is possible to package the substance in very small volumes, e.g. only 1 cm$^3$ of substance. This means that the dispensing assembly can be miniaturized. It also means that the substance used can be more concentrated, more active, and protected from the air. It can contain less preservative, thereby avoiding secondary effects with people who are allergic.

It should be observed with this first variant of the present dispenser device, that there is no air vent. Consequently the pressure inside the flask will gradually fall off, and may end up at around 0.5 atmospheres.

Apart from the spring, the other three component parts of the present dispenser device (the pump body 1, the rod-piston 3, and the endpiece 2) may be manufactured by injection molding a plastic selected as a function of the substance to be dispensed and also of the particular function of each of the components. However, when sealing is required between two parts that slide relative to each other, it becomes more difficult to find substances that satisfy these selection criteria. For example, in the pump body 1 it is desirable for the base to be relatively rigid in order to serve as an abutment for the spring 4, inter alia. However, it is also necessary to provide an enclosure 11 which is sufficiently flexible to bear closely against the head 31 of the piston 3 and guarantee sealing contact all around the line 11'. In order to satisfy these two requirements which are, a prior, contradictory, a second variant of the present device is proposed. This variant is illustrated in FIGS. 9 to 11.

Figures 9, 10, 11:
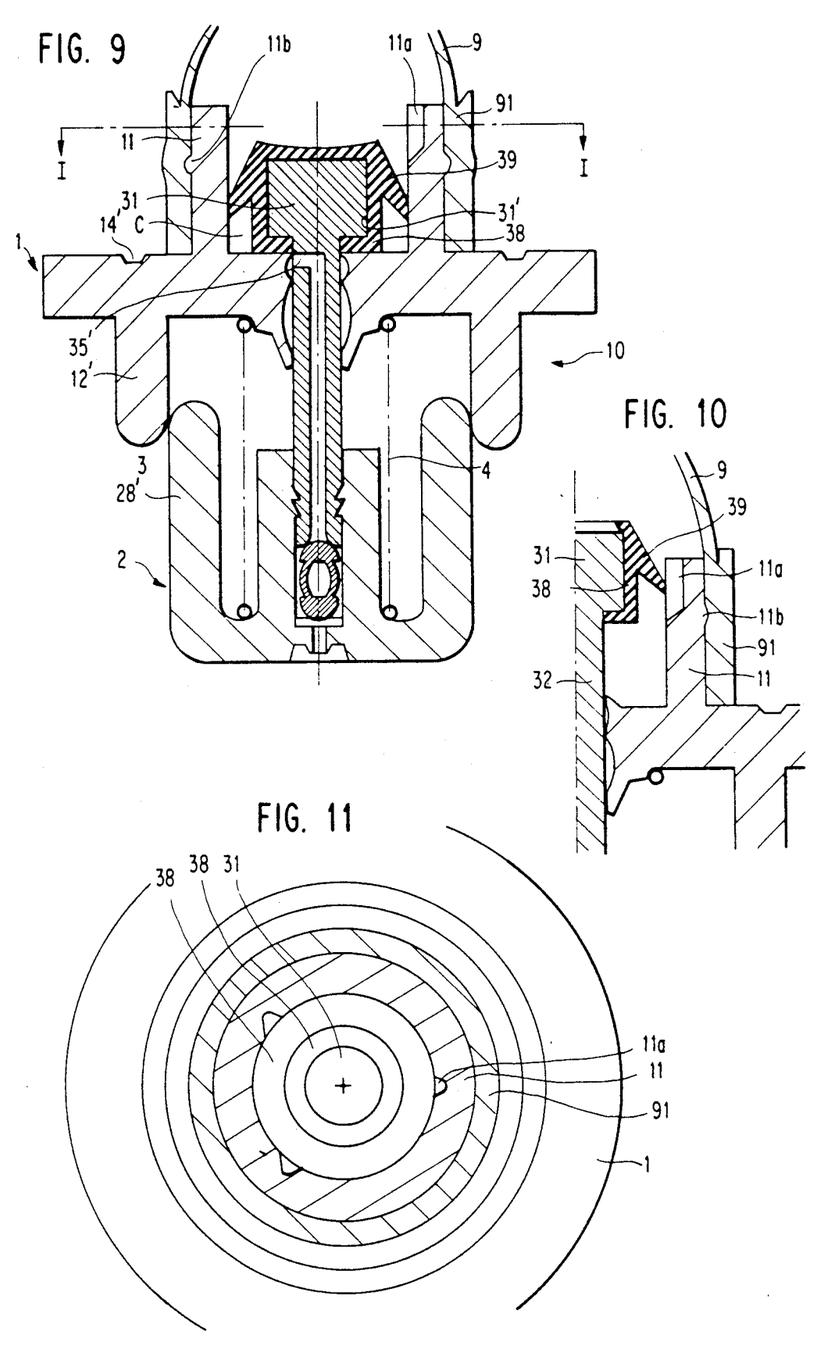
FIG. 9 is an axial section through a second variant of the dispenser device of the invention shown in its rest position.
FIG. 10 is a detail of the section of FIG. 9 but with the second variant of the dispenser device being shown in the high, admission position of the piston.
FIG. 11 is a cross-section on a plane I—I of FIG. 9 showing the second variant of the dispenser device as shown in the two preceding figures.

In particular, the axial section of FIG. 9 shows that this variant differs from the preceding variant essentially by interposing a gasket 38 between the sliding surface 31' of the piston head 31 and the enclosure 11. In order to facilitate assembly, the gasket 38 is in the form of a hollow cylinder having a bottom pierced by a hole. It is made of flexible plastic material and is thus suitable for being threaded onto the rod-piston 3, with the rod 32 being engaged in the hole. The height of the corresponding cylinder is then designed so that once the bottom thereof is fitted to the root of the head 31, the cylinder projects a little beyond the head. As a result, the flexible gasket 38 is firmly held on the piston 3. It can then be seen that the resulting assembly operates in the same way as the preceding rod-piston providing the opening 35' of the radial duct 35 is moved away from the root of the head 31 in order to avoid it being obstructed by the gasket 38.

The advantage of having such a gasket 38 is that by virtue of its shape and the material from which it is made it is easy to provide the gasket with a particularly effective sealing lip 39. The lip 39 is directed towards the bottom wall of the pump chamber C so that in collaboration with the enclosure 11 it provides sealing which increases with increasing pressure inside the chamber. As a result, there is no longer any need for the rod-piston 3 or the pump body 1 to be particularly flexible. The enclosure 11 can then be in the form of a relatively thick hollow cylinder projecting perpendicularly from the base of the pump body. This makes it much easier to mold.

In this case, it is necessary to provide one or more axial grooves 11a inside the enclosure 11 (cf. the cross-section of FIG. 11). These grooves 11a run from the open end of the enclosure 11 and extend to a greater or lesser extent down the inside wall of the enclosure 11. This makes it possible to adjust the effective stroke of the piston in that the sealing provided by the lip 39 ceases to have any effect once the lip lies over the grooves 11a. In other words, the volume of the chamber C that can be confined inside the enclosure 11 and which will give rise to a drop being expelled, is constituted merely by that portion of the volume of the enclosure 11 which corresponds to its groove-free height. By varying the height of the enclosure which does not have grooves, it is possible to vary the size of the drops as dispensed.

This disposition means that the same pump body 1 can be adapted to different sizes of drops to be dispensed, and it may be accompanied by additional measures for adapting the stroke of the piston. As can be seen in FIG. 10 which shows the high position of the piston, there is no need, in this embodiment of the dispenser device, for the head 31 to move fully out from the enclosure 11 in order to admit substance into the chamber C. On the contrary, the lip 39 must remain in contact with the inside wall of the enclosure 11, but once it lies over a groove 11a, the stroke may be stopped. Adjustable-height abutment means (not shown) may be disposed for this purpose between the pump body and the endpiece of the dispenser device.

Further, since it is now possible to mold the pump body 1 and thus the enclosure 11 using a more rigid plastic material, an advantageous variant may be developed. The enclosure 11 can then be used for fixing a pocket 9 over the top end of the dispenser device 10, with the pocket being constituted, for example, by a flexible elastomer membrane. To do this, the outside wall of the enclosure 11 is advantageously provided with an annular thickening 11b whereas the pocket 9 (visible only in part in FIGS. 9 and 10) has an opening 91 with a reinforced edge. Once this opening 91 has been passed over the enclosure 11, the resilience of the membrane constituting the pocket 9 will give a sealed connection and the thickening will prevent the pocket 9 from sliding off. As a result, the supply of substance contained in the pocket is protected from air while remaining at atmospheric pressure regardless of the number of drops that have been expelled. To make this possible, it suffices for the flask or housing (not shown) facilitating handling of the dispenser assembly to be fixed to the pump body in a non-sealed manner. Then, each time a drop is dispensed, air penetrates into the dispenser assembly and the pocket 9 shrinks. Where appropriate, other methods of fixing the pocket 9 to the enclosure 11 may be used, e.g. snap-fastening, welding, heat sealing, . . . .

In the detailed description below other variants of the various components of the present dispenser device are mentioned. Some of the features of these variants are already shown in FIGS. 9 to 11 described above. However, the description of the dispenser device per se is now terminated in favor of describing the assembly which, in the present invention, comprises not only the dispenser device but also a supply of substance to be dispensed and means for making it easy to handle. However, the person skilled in the art will understand that the various designs of pump body, endpiece, rod-piston, enclosure, etc. can be interchanged to a greater or lesser extent between the various embodiments described.

In some applications, the variants of the dispenser device 10 as described above suffer from a drawback. They are designed to be associated with a flask which is mounted in sealed manner or otherwise to the pump body. In addition, a handling housing is necessary in order to facilitate actuating the device which is very small in size because of the small volume of drops to be delivered. As a result, the dispenser assembly requires numerous operations during assembly by the manufacturer, and in particular:

1/ the flask must be filled;

2/ the pump body must be crimped onto the full flask; and

3/ the flask together with its pump needs installing in the handling housing.

When millions of dispenser assemblies are to be assembled in this way, these operations become a major drawback economically speaking. It would therefore be advantageous to reduce the number of operations, even if only by one.

Figure 12:
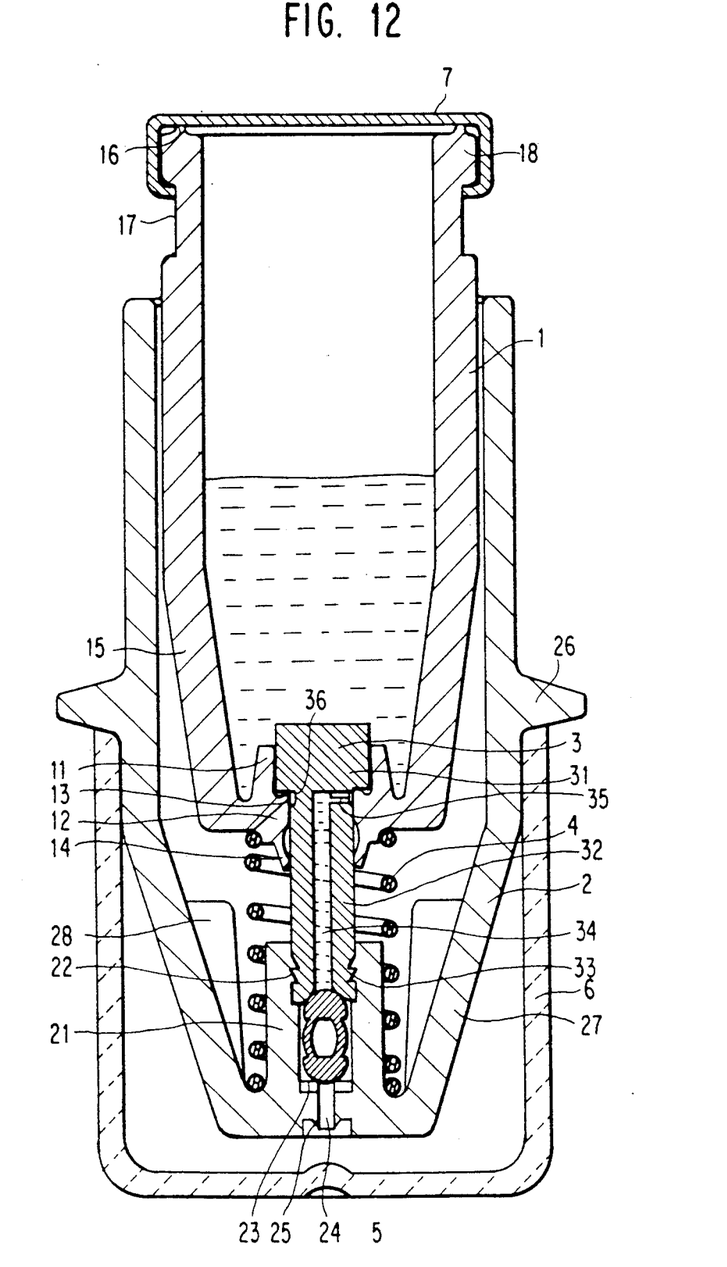
FIGS. 12 and 13 are axial sections through a second embodiment of the dispenser assembly of the invention shown respectively with the piston in its low, rest position and in its high position as reached when a user compresses the assembly to a maximum extent.

This is made possible by the second embodiment of a dispenser assembly of the present invention as shown in FIG. 12. It comprises a receptacle 1 which is advantageously made of relatively flexible plastic material such as low density polyethylene. The receptacle 1 is in the form of a right cylinder of arbitrary height. At one of its ends the cylinder is open with its edge 18 preferably having an axially-extending annular ridge 16. An annular groove 17 formed in the outside surface of the receptacle close to its edge 18 enables a capsule 7 (e.g. made of deformable metal) to be crimped around the edge 18, thereby closing the open end of the receptacle 1 in sealed manner.

At its opposite end, the receptacle 1 preferably tapers in the form of a truncated cone 15. At the bottom of the truncated cone 15 a thick annular lip projects into the receptacle. This lip constitutes the enclosure 11 for a pump chamber as in the previously-described variants of the device of the invention. However, in this case it forms a part of the receptacle 1 which now has the pump body integrally formed therewith. Concentrically with the enclosure 11 there is a hole passing through the bottom of the truncated cone 15. The wall 12 of this hole is advantageously provided with a very fine sealing lip 13 at its end inside the receptacle, and with a sealing sleeve 14 at its end outside the receptacle.

As in the structure of the variants described above, a rod 32 is passed through the hole in order to slide therein in sealed manner. The rod 32 is also fixed to a head-forming piston 31. The cross-section of the piston head is slightly greater than that of the rod in order to travel within the enclosure 11 while its sliding surface 31' remains in sealed contact with the enclosure 11. Like the first above-described variant, the enclosure 11 is somewhat flared at its base standing on the bottom of the truncated cone 15. This reduces the contact area between the piston and the enclosure 11, thereby enhancing good sealing.

The rod 32 is pierced by an axial channel 34. This channel communicates with a duct 35 opening out sideways in the surface of the rod 32 immediately adjacent to the base of the piston head 31. In this embodiment, a small annular cut-out 36 is provided around the rod 32 level with the outlet from the duct 35 and extending along a height which is hardly any wider than said opening. Thus, the fine sealing lip 13 disposed on the wall 12 of the hole through the bottom of the receptacle 1 is in no danger of being jammed in the opening of the duct 35 as the rod 32 moves up and down.

As in the first embodiment of the present assembly described above, the free end of the rod 32 is adapted to engage in a hollow tube 21 fixed to an endpiece 2. To this end, the rod 32 has a series of sharp projections 33 on its lateral surface, for example. These projections then co-operate with a complementary series of grooves 22 in the inside surface of the tube 21 when the rod 32 is forced into the free end of the tube 21. At its other end, the tube 21 has a bottom pierced by an orifice 24. Thus, between the bottom of the tube and the rod 32 there is a chamber, and in similar manner to the first variant described above of the dispenser device, this chamber receives a small part 5 acting as a non-return valve. This part is advantageously symmetrical in shape in order to facilitate installation thereof and is constituted, for example, by two hemispheres having one or more flexible spacers disposed therebetween. One hemisphere is then disposed to close the channel 34 in the rod 32 and the other to close the orifice 24 of the endpiece 2.

As shown in FIG. 12, the orifice 24 may be constituted merely by a hole through the bottom of the hollow tube 21 in the endpiece 2, together with radially disposed fluting 23 on the inside of the bottom, and an annular chamfered portion 25 set back in the outside surface. The advantage of this structure has also been described. It is returned to below when describing the operation of this second embodiment of the present dispenser assembly. For the time being, it is merely recalled that various types of conventional nozzle (spray nozzle, flow-cutting nozzle, ... ) can be fitted to the endpiece 2 over its orifice 24 in order to apply the present assembly to all sorts of utilizations.

The portion of the endpiece 2 described above already exists in the first embodiment shown in FIGS. 1 to 11. In this second embodiment, this part is made integral with an outer shell 27 which also serves as a pushbutton. The bottom of the tube 21 extends laterally around the tube flaring smoothly until it completely surrounds the right cylinder of the receptacle 1. Outside the shell 27 of the pushbutton/endpiece 2 there is an outwardly projecting grasping ring 26. Inside its flared length there are partitions 28. These partitions co-operate with the outside surface of the tube 21 for guiding a return spring 4 disposed axially between the pushbutton/endpiece 2 and the receptacle/body of the pump 1. Finally, a cap 6 is advantageously provided to be a force-fit over the shell 27 of the pushbutton/endpiece 2 for the purpose of protecting its orifice 24.

The dispenser assembly whose structure is described above is generally delivered to the manufacturer of the substance to be dispensed, e.g. a pharmaceutical manufacturer, without its capsule 7. The manufacturer then pours substance into the receptacle/pump body 1 while the pump is pointing downwards. It is preferable for the quantity of substance poured in in this way to be limited to one half the capacity of the receptacle. Thereafter, the manufacturer crimps on the capsule 7 without changing the orientation of the dispensing assembly. After these two operations only, the assembly is ready for delivery to the end user.

The user in question may be a patient who needs to administer the product one drop at a time. Some eye treatments require doses to be administered which are only just large enough to spread over the surface of the eye, thereby avoiding any excess substance being eliminated via the tear duct. In this case, the user removes the cap 6 and holds the dispenser assembly between three fingers, with the thumb and middle finger advantageously bearing against the ring 26 of the pushbutton/endpiece 2 while the index finger bears against the bottom of the capsule 7. The assembly is held with its orifice 24 pointing down.

Thereafter the dispenser assembly is operated in much the same manner as the first embodiment of the present invention. When the user presses the receptacle/pump body 1 into the pushbutton/endpiece 2, the endpiece guides the receptacle, the return spring 4 is compressed and the rod-piston 3 rises inside the receptacle. The piston 31 the tends to move out from the enclosure 11 defining the pump chamber C and the free space between the base of the piston 31 and the bottom of the truncated cone 15 increases. The opening of the duct 35 simultaneously disengages the fine sealing lip 13. Assuming that the pump is primed, i.e. that the channel 34 is already full of substance, the pressure of that substance is reduced as the volume of the pump chamber increases.

This continues until the receptacle/pump body 1 comes into abutment against the partitions 28 in the pushbutton/endpiece 2. The dispenser assembly is then in the position shown in FIG. 13. It can be seen therein that in this case the length of the rod 32 is adjusted relative to the stroke of the receptacle 1 in the endpiece 2 in such a manner that the piston 31 escapes fully from the enclosure 11 defining the pump chamber C. With the corresponding opening of the admission valve, the relative suction created in the pump chamber causes substance to be sucked into the pump chamber. Assuming that the enclosure 11 is immersed in the substance, the substance penetrates into the chamber and fills it. It should be observed that during the events described above the non-return valve 5 remains closed and isolates all of the substance from the outside.

Figure 13:
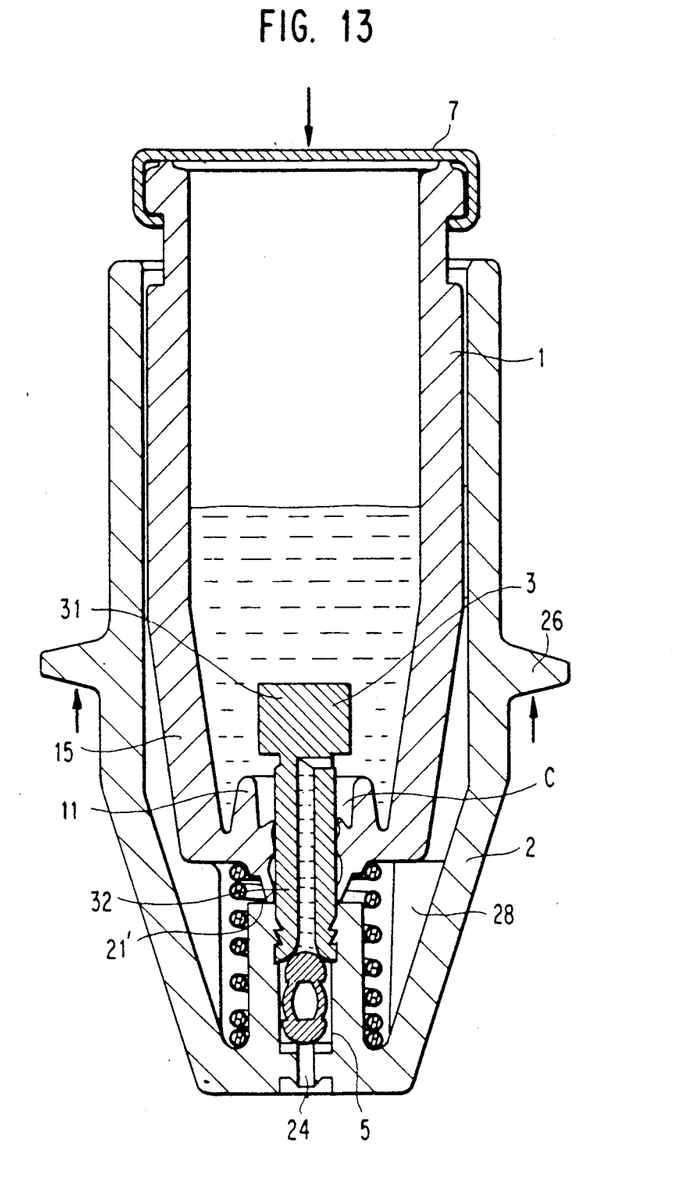

Then, when the user releases the force on the receptacle, thereby allowing the return spring 4 to expand, the piston 32 re-engages inside the enclosure 11. By virtue of the seal which is re-established between the enclosure and piston, the admission valve is reclosed, and the pump chamber C is isolated again. Immediately thereafter, its volume constituted by the space inside the enclosure 11 between the base of the piston 31 and the bottom of the truncated cone 15 of the receptacle/pump body 1 begins to shrink. This increases the pressure of the product trapped inside the chamber. The flexibility of the lip 13 at the bottom of the truncated cone 15 of the receptacle/pump body 1 prevents any of the substance from leaking under pressure between the wall 12 and the rod 32. Indeed, the pressure in the chamber urges the lip 13 against the rod 32 over a relatively large area.

During this transient stage, the opening of the duct 35 is unobstructed so the pressure of the substance is communicated to the non-return valve 5. Given the way the valve is designed, it opens for a pressure which is only slightly greater than atmospheric pressure. Even so this suffices to guarantee that the product is emitted with a certain amount of force. The fluting 23 completes division of the product prior to it being expelled via the orifice 24 of the pushbutton/endpiece 2. The chamfered end 25 of the orifice 24 also ensures that the drop becomes detached as soon as the dimensions described relative to the first embodiment of the present dispenser assembly are satisfied.

That is how the rest position shown in FIG. 12 is rapidly re-established. The volume of liquid expelled by the dispenser device sets up or increases suction in the receptacle. In practice this is not particularly inconvenient in that a sufficiently large quantity of air is present initially (in general about half its capacity). In this case, emptying the receptacle leads to a final pressure of about half a bar and this is perfectly compatible with overall sealing of the receptacle, given that it has a sleeve 14. This pressure difference is insufficient to lift the enclosure 11 off the piston 31 or to lift the lip 13 off the opening to the duct 35. As a result the channel 34 remains filled with liquid so that next time the device is operated a drop is properly delivered. However, in order to provide greater security, particularly once the dispenser assembly has aged somewhat, the lip 13 is maintained in a curved position against the base of the piston 31 when the device is in its rest position. The creep to which the lip is subjected over time therefore tends to provide sealing which is increasingly effective.

However, priming this second embodiment as described above requires pump chamber dimensions to satisfy conditions, as for the first embodiment. The first time the device is actuated, with the channel 34 still filled with air, less suction is established in the chamber C. After its admission valve has opened, it is filled mostly under gravity and air is not expelled to any great extent from the channel 34. Priming is therefore possible only if the maximum content of the chamber is sufficiently large relative to the content of the channel. In practice this sets a bottom limit on the size of drops dispensed to around 5 microliters. Below this value, the air initially contained in the channel 34 can compress to provide room for the substance coming from the pump chamber without establishing sufficient excess pressure to open the outlet valve 5.

However, in the context of the present invention, this limitation can be overcome. The dispenser assembly as shown in FIGS. 12 and 13 may be filled while the admission valve is open. The manufacturer of the liquid does this by disposing the assembly in a receptacle which keeps the return spring 4 compressed. While the piston 31 remains disengaged from the enclosure 11 in this way, substance enters the channel 34 and remains trapped therein as soon as the spring 4 is relaxed again. However, it is nevertheless necessary to ensure that the receptacle/pump body 1 is filled with substance under a small amount of pressure in order to ensure that the air initially present in the channel 34 is expelled, unless the channel is large enough for capillary tension effects to be avoided.

Figure 14:
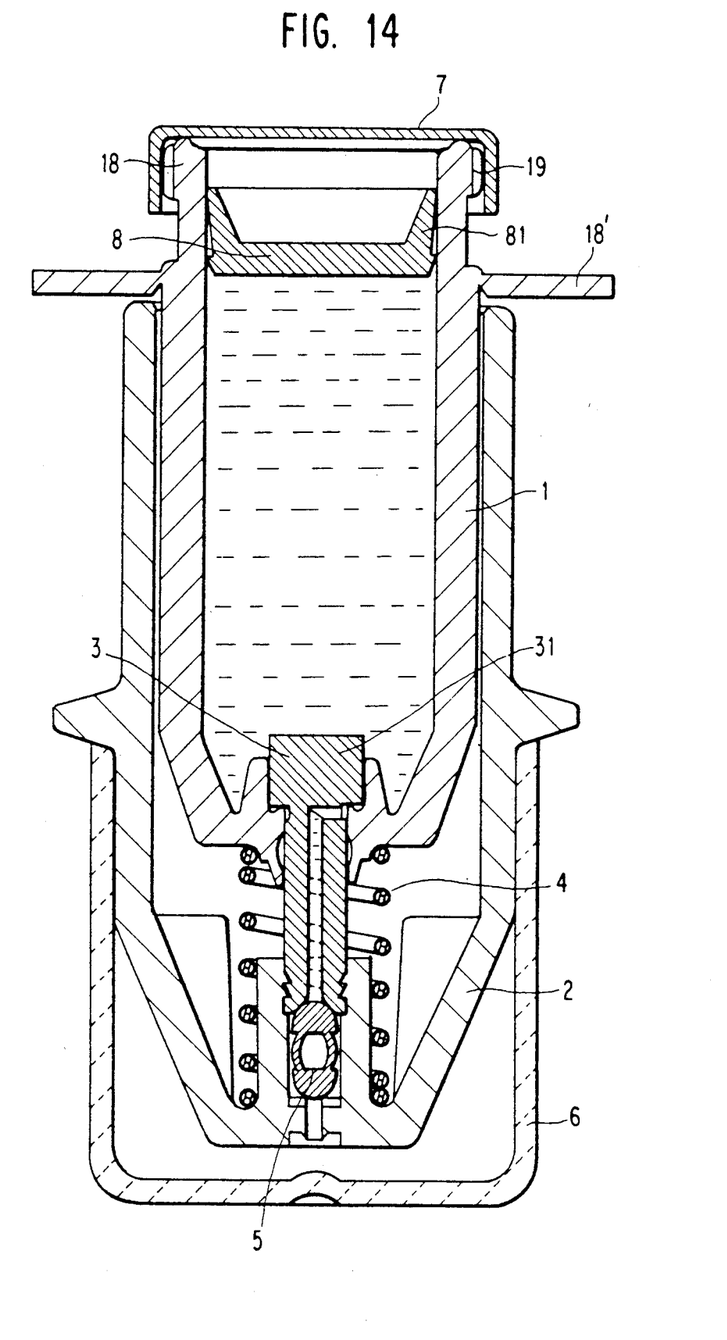
FIGS. 14 and 15 are axial sections respectively through a third and a fourth embodiment of the present assembly (shown each time in the rest position).

A third embodiment of the present dispenser assembly is shown in axial section and in the rest state in FIG. 14. It differs from the preceding assembly in its system for closing the receptacle/pump body 1. This time, the substance to be dispensed is enclosed therein without air, and a scraper piston 8 is used to close the open end of the receptacle. A cap 7 is snap-fastened over said end and the rim 18 of the end includes notches 19 for admitting air. Thus, a thrust surface is provided for actuating the dispenser assembly while the scraper piston 8 moves further and further into the receptacle as it is emptied. This means that it is no longer essential to keep the pump at the bottom of the dispenser assembly in order to ensure that a drop of substance is ejected.

This third embodiment is advantageous when the substance to be dispensed needs to be kept separate from the air in order to avoid chemical damage, etc. However, compared with the second assembly described above, it leads to a larger quantity of substance being lost. When the scraper piston 8 comes into contact with the piston 31, the dispenser device can no longer be actuated. Thus, any substance remaining around the piston 31 cannot be extracted from the receptacle. If there were no scraper piston 8, then the substance could be extracted from the pump until the liquid level drops below the edge of the enclosure 11. The truncated cone shape 15 of the receptacle/pump body 1 also serves to reduce the quantity of substance remaining in the dead volume to a minimum. To the same end, it is possible to give the scraper piston 8 a shape which is complementary to that of the piston 31.

In the last two embodiments described above, tamper-proofing tongues 18' can be molded on the receptacle/pump body 1 as shown in FIG. 14. Although easily sheared off, these tongues 18' withstand compression well. Thus, until a user tears them off deliberately, they prevent the dispenser assembly being used by providing an abutment for the pushbutton/endpiece 2. Similarly, they make it much easier for the manufacturer of the substance to be dispensed to crimp on the capsule or snap on the cap.

Finally, it will be understood that the height of the receptacle 1 and its endpiece 2 are arbitrary, a priori. In particular, it would be quite possible for the receptacle to be pipette-shaped.

Figure 15:
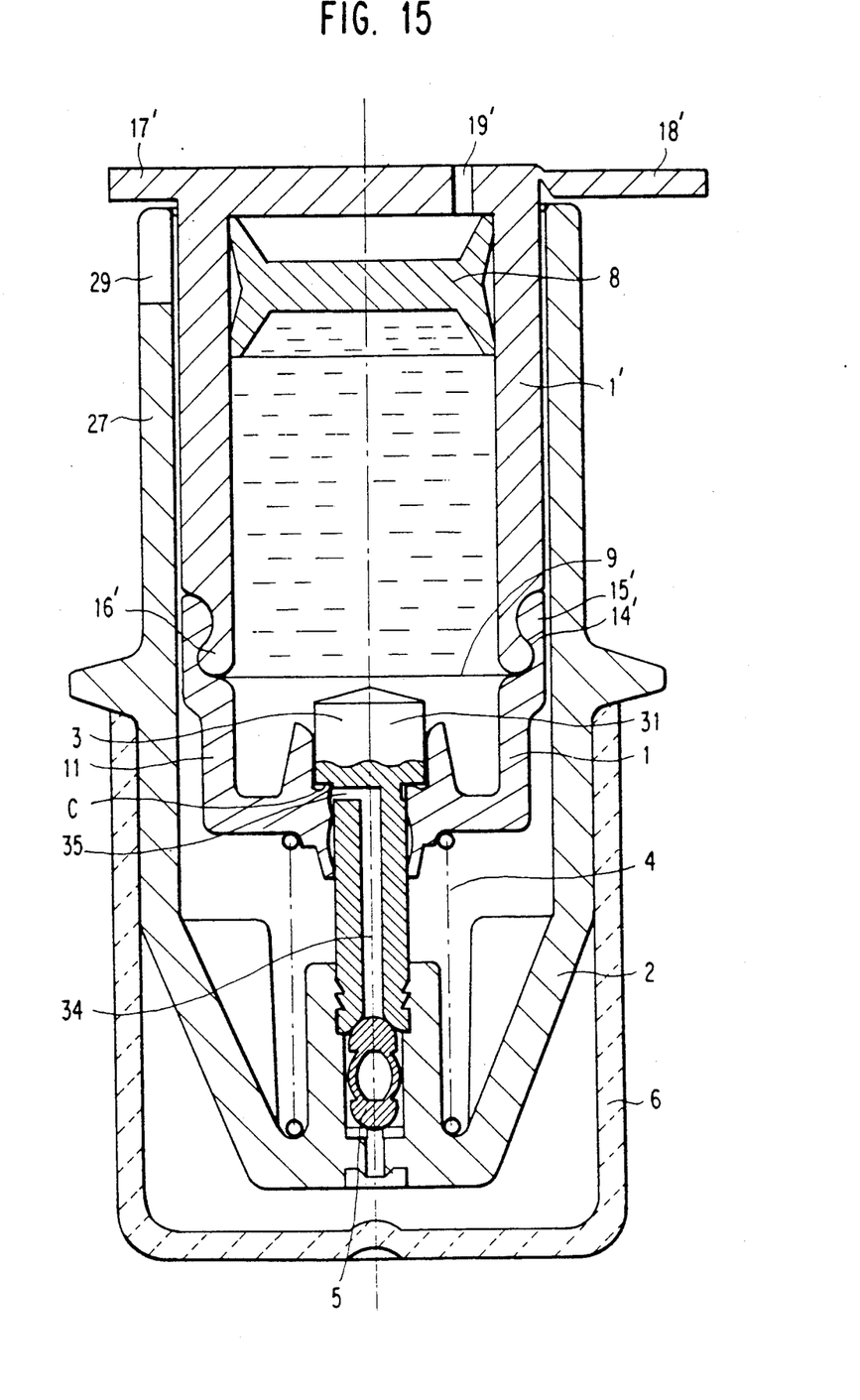

A fourth and last embodiment of the present dispenser assembly in shown in axial section in FIG. 15. Apart from one or two minor modifications, its moving parts (reference numerals 2 to 6) are identical to those of the second and third embodiments of FIGS. 12 to 14. Its novelty lies in the supply of substance. In this case, the supply is in the form of a cylindrical cartridge 1 having one end 16' which is both closed by a diaphragm 9 and provided with lateral projections for snap-fastening purposes. The opposite end of the cartridge 1' is in the form of a bottom. However, the bottom is pierced by an air inlet hole 19'. It may also be provided with a tear-off tamperproofing tongue 18' projecting locally from its periphery. Similarly, a lateral safety tab 17' may be provided. Inside the cartridge 1' there may be a scraper piston 8 for hermetically isolating the substance to be dispensed from ambient air.

It will be understood how the manufacturer of the substance to be dispensed finds such a cartridge 1 constitutes an advantage for packaging purposes. To begin with the scraper piston 8 is placed inside an empty cartridge. This is generally easier to do than inserting a piston over the substance and then crimping on a capsule or snapping on a cap as required by the third embodiment described above (cf. FIG. 14). Thereafter, the substance is poured into the cartridge 1'. Finally a diaphragm 9 is applied to the open end 16' of the cartridge. This operation may be performed by heat sealing, for example, but other methods of closing the end 16' by a diaphragm 9 are also possible. Thereafter, the filled cartridge 1' is easily snap-fastened in a pump body 1 as described above with respect to the second embodiment of the present assembly, for example. To do this, it suffices for the pump body 1 to have an edge 15' provided with an annular groove 14' for co-operating with the snap-fastening projections at the end 16' of the cartridge 1'. It is nevertheless important that the snap-fastening should provide adequate sealing.

The end user uses this fourth embodiment of the present assembly in the same way as the preceding embodiments. The tamperproofing tongue 18' is torn off and the cap 6 is removed. Then, e.g. using the index finger, the accessible end of the cartridge 1' projecting from the endpiece 2 is pressed down. Providing the lateral safety tab 17' is indeed disposed facing a notch 29 formed in the endpiece 2, the spring 4 can then be compressed and the moving parts of the assembly (i.e. the endpiece 2, the rod-piston 3, and the non-return valve 5) are displaced relative to the pump body 1. As described in greater detail above, the piston head 31 moves out from the enclosure 11 defining the pump chamber C. The top of the head 31 is deliberately shaped as a punch in this embodiment and it bursts the diaphragm 9. The substance then spreads into the pump body 1 and penetrates into the enclosure 11 while the air initially trapped in the body 1 rises beneath the scraper piston 8.

So long as the relative sizes of the chamber C at its greatest extent and of the axial channel 34 and the radial duct 35 specified above are satisfied, then the dispenser device of the invention will prime. As the substance is dispensed, the scraper piston 8 moves down inside the cartridge 1' with air admitted via the hole 19' compensation for the drops of substance dispensed. Each time the device is actuated, it is advantageous for the user to rotate the cartridge 1' a little relative to the shell 27 of the endpiece 2. This moves the lateral safety tab 17' away from the notch 29, thereby preventing relative axial movement between the various parts constituting the dispenser assembly of the invention.

Numerous other variants will appear to the person skilled in the art depending on the intended application and without thereby going beyond the scope of the present invention as specified by the following claims.

We claim:

1. A dispenser device for dispensing a liquid or cream type substance in the form of small volume drops, the device comprising:

a pump body having a pump chamber formed therein with a bottom wall and an enclosure whose end furthest from said bottom wall is open;

a piston adapted to engage an inside of said enclosure via said open end and to slide in sealed manner therein between a high, admission position for admitting said substance into said chamber and a low, rest position, said piston being fixed to a rod of smaller diameter which passes in a sealed manner through said bottom wall of said chamber and has a free end extending outside said pump body, said rod being pierced by a central channel communicating with a duct opening out laterally beneath said piston;

an endpiece having a dispensing orifice and adapted to be fastened in a sealed manner to said free end of said rod extending outside said pump body in such a manner that said central channel faces said orifice;

resilient means disposed between said pump body and said endpiece for returning said piston to said low, rest position in which it comes into abutment against said bottom wall of said chamber; and an outlet valve disposed between said central channel of said rod and said dispensing orifice of said endpiece.

2. A dispenser device according to claim 1, wherein said enclosure flares from its open end towards said bottom wall of said chamber such that once said piston engaged in said enclosure, sealing contact is established around a line only, said duct opening out at the root of said piston.

3. A dispenser device according to claim 1, wherein said dispensing orifice forms a portion of a nozzle integrated in said endpiece.

4. A dispenser device according to claim 1, wherein the maximum volume of said pump chamber, equal to the product of the section of said piston multiplied by its stroke, i.e. the distance between its high position and its low position, is greater than the sum of the volume of said central channel and said radial duct of said rod.

5. A dispenser device according to claim 1, wherein the volume of a delivered drop lies in a range of from 5 mm³ to 25 mm³.

6. A dispenser assembly including a dispenser device according to claim 1, wherein said pump body is adapted to receive in sealed manner and by snap-fastening a cartridge having a bottom and an open end opposite to said bottom, an air vent being provided through said bottom, a supply of said substance initially being contained inside said cartridge between a diaphragm closing said open end and a scraper piston disposed adjacent to said bottom, said piston also having a punch-forming face suitable for puncturing said diaphragm on the first occasion said dispenser device is actuated.

7. A dispenser device according to claim 1, wherein said pump body includes a sealing sleeve directed towards the outside of said body in order to bear against said rod passing through said bottom wall of said chamber.

8. A dispenser device according to claim 7, wherein said pump body is made of a plastic material whose flexibility is comparable with that of low density polyethylene, said body also including a fine sealing lip directed towards the inside of said chamber in order to bear against said rod passing through said bottom wall, said rod having an annular cut-out into which said lateral duct opens out.

9. A dispenser assembly including a dispenser device according to claim 1, wherein said pump body is crimped onto a flask which has a bottom and which encloses a supply of said substance protected from the air.

10. A dispenser assembly according to claim 9, wherein said endpiece extends around said rod of said piston in the form of a shell suitable for receiving said supply of said substance while leaving said bottom disengaged, said shell including grasping means, thereby enabling a user to apply two fingers of one hand thereagainst while pressing with another finger of the same hand against said bottom so as to actuate said dispenser device.

11. A dispenser assembly according to claim 9, wherein a housing receives said dispenser device together with said supply of substance, said housing being adapted to leave said dispensing orifice disengaged and also to leave said bottom disengaged, and being of such a shape as to enable a user applying two fingers of one hand against said housing to be able to press against said bottom with another finger of the same hand in order to actuate said dispenser device.

12. A dispenser assembly according to claim 11, wherein said bottom initially includes tear-off tamper-proofing tongues projecting laterally in order to constitute an abutment for said supply and prevent said dispenser device being actuated.

13. A dispenser assembly including a dispenser device according to claim 1, wherein said pump body extends around said enclosure defining said pump chamber to constitute a receptacle which is open at its end furthest from said pump body in order to receive a supply of said substance protected from the air, said end of said receptacle being closed by closure means for forming a bottom on said dispenser assembly.

14. A dispenser assembly according to claim 13, wherein said receptacle flares away from said enclosure to constitute a truncated cone such that there exists a minimum inside volume between said receptacle and said enclosure.

15. A dispenser assembly according to claim 13, wherein said closure means of said receptacle are constituted by a capsule which is crimped on after said receptacle has been filled to about one half its capacity with the substance.

16. A dispenser assembly according to claim 13, wherein said closure means of said receptacle are constituted by a snap-on cap, with an air vent being provided between said open end of said receptacle and said cap, and a scraper piston also being engaged in sealed manner inside said receptacle in order to separate said substance from the ambient air regardless of how full said receptacle may be.

17. A dispenser device according to claim 1, wherein said endpiece comprises a hollow tube having an open end, said free end of said rod being adapted to snap-fasten within said open end of said hollow tube.

18. A dispenser device according to claim 17, wherein said outlet valve occupies the bottom of said hollow tube in said endpiece and is constituted by two identical hemispheres with at least one flexible spacer extending therebetween, one of the hemispheres co-operating with the opening of said central channel, and the other hemisphere co-operating with said dispensing orifice.

19. A dispenser device according to claim 17, wherein said resilient means are constituted by a helical spring and wherein said endpiece also includes an outer annular wall for holding and fixing said spring around said hollow tube.

20. A dispenser device according to claim 19, wherein said high position of said piston is determined by the said free end of said hollow tube of said endpiece coming into abutment against said pump body.

21. A dispenser device according to claim 17, wherein said resilient means are constituted by a helical spring and wherein said spring is held around said hollow tube by radial partitions integral with said endpiece.

22. A dispenser device according to claim 21, wherein said high position of said piston is determined by said radial partitions integral with said endpiece coming into abutment against said pump body.

23. A dispenser device according to claim 1, wherein said enclosure is a right cylinder, said piston being enveloped by a flexible cylindrical gasket provided on its outside with an annular sealing lip directed towards said bottom wall of said chamber such that said lip co-operates with said enclosure in order to delimit said pump chamber, with at least one groove extending axially inside said enclosure from said open end down to a height such that said lip faces said at least one groove when said piston is in its high, admission position.

24. A dispenser device according to claim 23, wherein said gasket has a bottom pierced by a hole adapted to receive said rod, said duct opening out laterally beneath said bottom of said gasket, and wherein said gasket extends beyond said piston so that said gasket is firmly retained on said piston.

25. A dispenser device according to claim 23, wherein abutment means are disposed between said pump body and said endpiece in order to limit the stroke of said piston between its low, rest position and its high, admission position.

26. A dispenser device according to claim 23, wherein a flexible pocket is fixed in sealed manner around said enclosure in order to receive a supply of said substance and protect it from the air.

27. A dispenser device according to claim 26, wherein said enclosure has an external annular thickening and wherein said pocket has an opening with a reinforced edge, said opening being adapted to engage in a sealed fit around said enclosure.

* * * * *